United States Patent
Lesniak et al.

(10) Patent No.: US 6,830,051 B1
(45) Date of Patent: Dec. 14, 2004

(54) INTEROCCLUSAL APPLIANCE

(75) Inventors: Frank Lesniak, Lansdale, PA (US); Michael S. Lesser, Green Brook, NJ (US)

(73) Assignee: Dental Concepts LLC, Paramus, NJ (US)

(*) Notice: Subject to any disclaimer, the term of this patent is extended or adjusted under 35 U.S.C. 154(b) by 28 days.

(21) Appl. No.: 10/425,908

(22) Filed: Apr. 29, 2003

(51) Int. Cl.⁷ ................................. A61C 5/14
(52) U.S. Cl. .............. 128/859; 128/861; 128/862
(58) Field of Search ..................... 128/846, 848, 128/859–862; 602/902; 433/6

(56) References Cited

U.S. PATENT DOCUMENTS

| | | |
|---|---|---|
| 3,247,844 A | 4/1966 | Berghash |
| 3,496,936 A | 2/1970 | Gores |
| 3,505,995 A | 4/1970 | Greenberg |
| 4,063,552 A | 12/1977 | Going et al. |
| 4,668,188 A | 5/1987 | Wolfenson et al. |
| 4,761,136 A | 8/1988 | Madhavan et al. |
| 4,776,792 A * | 10/1988 | Wagner .................. 433/71 |
| 4,955,393 A | 9/1990 | Adell |
| 5,305,741 A * | 4/1994 | Moles .............. 128/207.14 |
| 5,328,362 A | 7/1994 | Watson et al. |
| 5,339,832 A | 8/1994 | Kittelsen et al. |
| 5,406,963 A | 4/1995 | Adell |
| 5,566,684 A | 10/1996 | Wagner |
| 5,646,216 A | 7/1997 | Watson et al. |
| 5,746,221 A | 5/1998 | Jones et al. |
| 5,829,441 A * | 11/1998 | Kidd ........................ 128/859 |
| 6,036,487 A | 3/2000 | Westerman |
| 6,082,363 A | 7/2000 | Washburn |
| 6,302,686 B1 | 10/2001 | Chott et al. |

FOREIGN PATENT DOCUMENTS

EP 0 359 135 * 3/1990

* cited by examiner

Primary Examiner—Michael A. Brown
(74) Attorney, Agent, or Firm—Seth Natter; Natter & Natter

(57) ABSTRACT

An interocclusal appliance includes a maxillary impression preform of a resilient thermoplastic having a low softening temperature, e.g. 36° C., such as an EVA copolymer having approximately thirty percent vinyl acetate. The preform is molded over and unitarily bonded to a base having a planar bottom face contacted by mandibular occlusal surfaces. The base is formed of a thermoplastic having a higher softening temperature, e.g. 70° C., with the bond between the preform and base characterized by high shear strength. The preform includes a bight shaped centric relation positioning channel having a thick footing and draft along lingual, buccal and labial walls. The appliance is fitted by immersion in hot water to soften the preform, seating the maxillary arch within the channel and biting, such that the impression of the maxillary dentition embeds in the softened preform. Upon cooling, the preform is transformed into a reusable resilient encasement for the maxillary dentition. Suitable thermoplastics for implementation as the base include an EMA copolymer, blends of EMA and EVA or TPU or blends of TPU and EVA.

17 Claims, 3 Drawing Sheets

INTEROCCLUSAL APPLIANCE

BACKGROUND OF THE INVENTION

1. Field of the Invention

This invention relates generally to the subconscious parafunctional mandibular habits known as bruxism or clenching and more particularly an interocclusal appliance for the prevention of tooth structure loss resulting therefrom.

2. Antecedents of the Invention

Various studies have been undertaken with respect to the causative factors and precise mechanisms involved in bruxism and clenching. For example, it has been found and that bruxing events could be categorized based on mandibular position patterns.

Studies have also demonstrated that the highest amplitude of nocturnal bite force during bruxism could exceed the amplitude of the maximum voluntary bite force during the daytime. Bruxism and clenching have been found to constitute a major factor in conjunction with occlusal surface wear and constitute a significant potential risk factor for implant failure.

Interocclusal appliances, such as nightguards, have been long recognized as beneficial for the alleviation of the adverse effects of bruxism and clenching.

Prior interocclusal appliances included those fitted by a dental professional and those which were self fitted. Professionally fitted interocclusal appliances were molded of relatively hard acrylic resin from casts of the patient's mouth taken from a dental impression. This procedure was both time consuming and expensive.

A typical self fitted interocclusal appliance included a thermoplastic channel trough in the configuration of a maxillary arch. Carried in the trough was a thermoplastic impressionable liner material having a softening point temperature lower than that of the trough. The liner was molded to conform to the mouth of the user after the appliance was immersed in hot water and then inserted into the mouth, with the liner placed against the maxillary arch. The user's jaw was then closed and biting pressure was applied to force the maxillary teeth into the liner.

Problems which were encountered with respect to self fitting nightguards included those related to the fitting procedure itself and to the durability of the appliance. The inability to properly center and align, i.e. register, the heated impressionable liner material of the nightguard relative to one's own maxillary arch constituted a major deficiency. When the nightguard was not properly registered, an improper fit was obtained, resulting in discomfort as well as premature appliance wear.

Further problems were encountered with respect to the structural integrity of self fitting nightguards. As a result of the shear forces which were generated during bruxing or clenching events, separation of the bond between the liner and the trough occurred. With the trough in contact with the mandibular occlusal surfaces and the maxillary teeth embedded in the liner, lateral, superior and anterior mandibular deviations during bruxing events resulted in shear stress which separated the liner from the trough, rendering the appliance unserviceable.

SUMMARY OF THE INVENTION

A self fitting interocclusal appliance includes a base having a generally planar, smooth, occlusal face and a pair of parallel curved side walls. The base is molded of a thermoplastic having a Vicat softening temperature of at least 65° C. and a Shore A hardness of at least 80.

Molded into the base between and above the side walls is an impression preform comprising an EVA copolymer having approximately thirty percent vinyl acetate, a Vicat softening temperature of approximately 36° C. and a Shore A hardness below 80.

The preform includes a thick footing having a planar upper face and a shallow bight shaped centric relation pilot channel defined by peripheral walls which are sloped downwardly and inwardly from an elevation above the side walls of the base. The upper face of the footing defines the bottom of the pilot channel.

The base and preform are bonded to form a unitary appliance which is fitted by immersion in hot water such that the preform copolymer reaches a temperature above its softening temperature yet which can be comfortably withstood by oral tissue. The appliance is thereafter inserted in the oral cavity with the centric relation pilot channel substantially registered with the teeth of the maxillary arch. Light pressure is applied to seat the maxillary occlusal surfaces in the shallow preform pilot channel, after which biting pressure is applied to imbed the maxillary teeth in the preform footing.

Since the softening temperature of the base thermoplastic was not attained during the heating step, significant deformation of the base is avoided and the upper and lower occlusal surfaces are separated by at least the thickness of the base.

Upon cooling to oral cavity temperature, the preform is transformed into a reusable resilient flexible encasement for the maxillary dentition (maxillary encasement), with the appliance to be removed during day time hours and reused at bed time.

Suitable thermoplastics for employment as the preform include ELVAX® EVA copolymer and suitable thermoplastics for employment as the base include ELVALOY® EMA copolymer, ELVALOY® EMA blended with ELVAX® EVA or ELVALOY® EMA blended with PELLETHANE® TPU elastomer.

From the foregoing compendium, it will be appreciated that it is an aspect of the present invention to provide an interocclusal appliance of the general character described which is not subject to the disadvantages of the antecedents of the invention aforementioned.

A feature of the present invention is to provide an interocclusal appliance of the general character described which is particularly well adapted for self fitting.

It is a consideration of the present invention to provide an interocclusal appliance of the general character described which is well-suited for economical mass production fabrication.

Another aspect of the present invention is to provide an interocclusal appliance of the general character described which is configured for accurate centric relation self fitting.

A further feature of the present invention is to provide an interocclusal appliance of the general character described which reduces stresses imposed on tooth surfaces during bruxing events.

Another consideration of the present invention is to provide an interocclusal appliance of the general character described which is safe and easy to use.

Yet another aspect of the present invention is to provide an interocclusal appliance of the general character described suited for extended usage without deterioration.

To provide an interocclusal appliance of the general character described having a base and an impression material unitarily molded thereto and characterized by a high shear resistance bond between components is a still further consideration of the present invention.

Another feature of the present invention is to provide an interocclusal appliance of the general character described which prevents loss of tooth structure otherwise resulting from bruxing events.

Another aspect of the present invention is to provide an interocclusal appliance of the general character described which is uninhibiting and comfortable to wear.

To provide an interocclusal appliance of the general character described which reduces compressive and lateral forces upon individual tooth surfaces occurring during bruxing events is a still further consideration of the present invention.

A further feature of the present invention is to provide an interocclusal appliance of the general character described which promotes restful sleep.

Further aspects, features and considerations of the present invention in part will be obvious and in part will be pointed out hereinafter.

With these ends in view, the invention finds embodiment in the various combinations of elements, arrangements of parts and series of steps by which the aforesaid aspects, features and considerations and certain other aspects, features and considerations are attained, all with reference to the accompanying drawings and the scope of which will be more particularly pointed out and indicated in the appended claims.

BRIEF DESCRIPTION OF THE DRAWINGS

In the accompanying drawings in which is shown some of the various exemplary embodiments of the invention.

DESCRIPTION OF THE PREFERRED EMBODIMENTS

Figure 1:
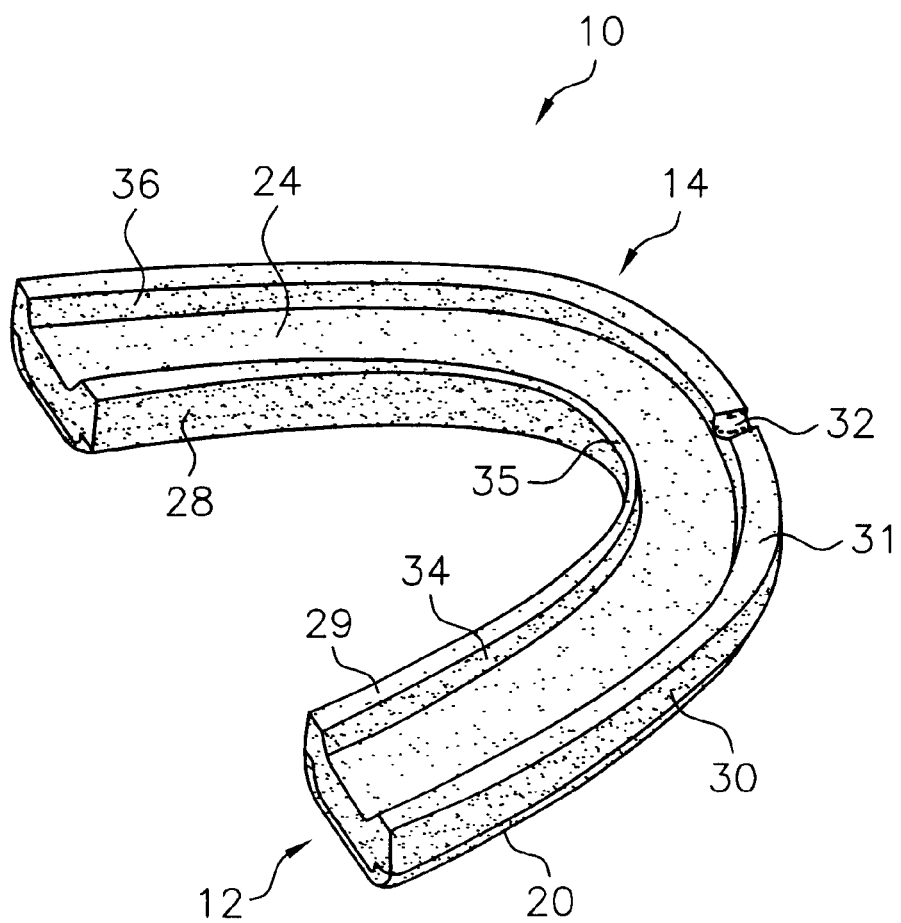
FIG. 1 is a perspective illustration of an interocclusal appliance constructed in accordance with and embodying the invention showing an impression preform having a shallow pilot channel molded over a base.
Figure 2:
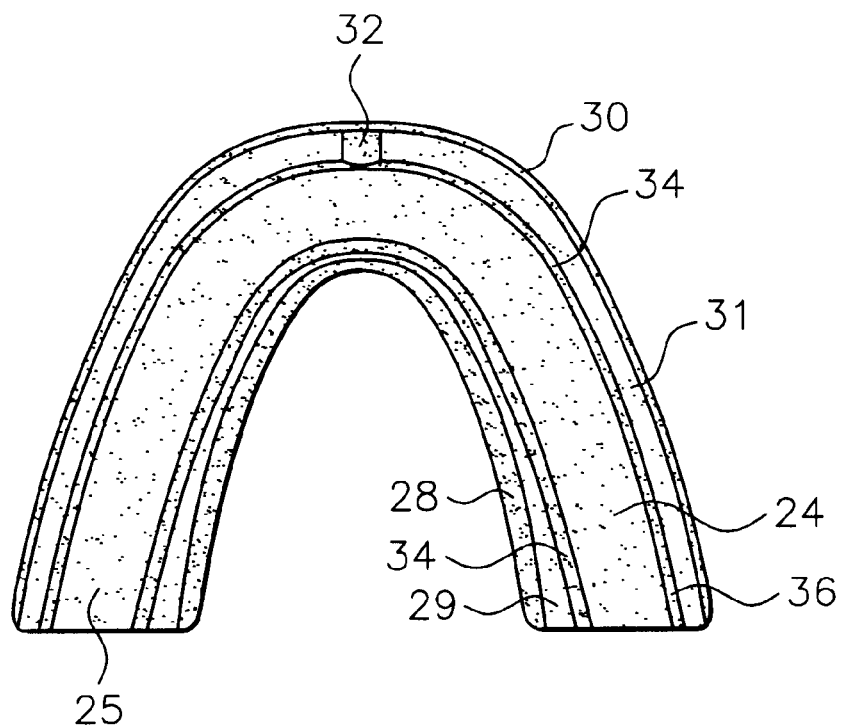
FIG. 2 is a top plan view of the interocclusal appliance, illustrating the impression preform.
Figure 3:
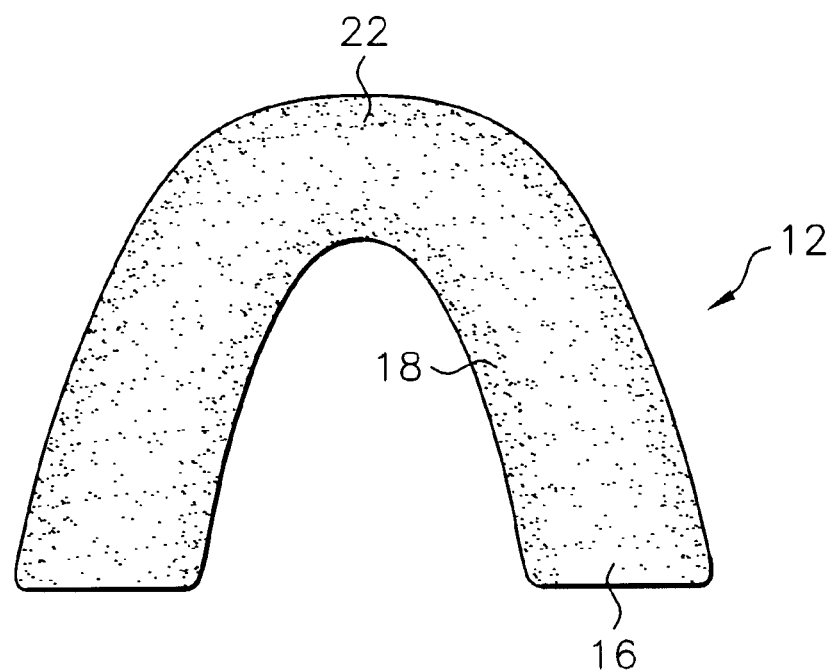
FIG. 3 is a bottom view of the appliance, showing a smooth occlusal face of the base.
Figure 4:
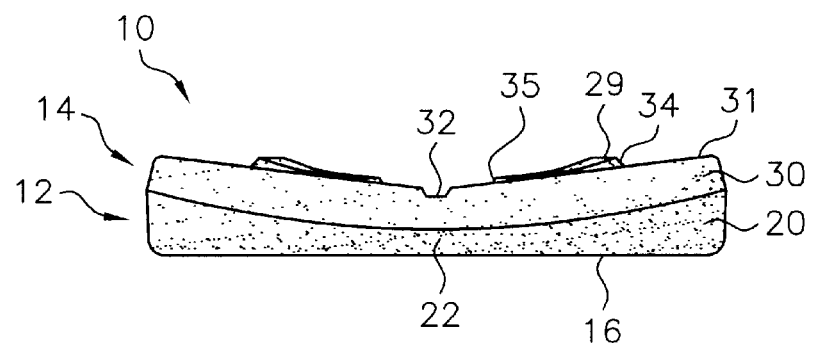
FIG. 4 is a front elevational view of the interocclusal appliance, illustrating a labial face of the base and a buccal peripheral wall of the impression preform.

Referring now in detail to the drawings, the reference numeral 10 denotes generally an interocclusal appliance constructed in accordance with and embodying the invention. The appliance 10 includes a lower base 12 having a plan configuration in the general shape of a maxillary dental arch. Molded to the base 12 is an impression preform 14. The impression preform 14 is transformed into a maxillary dentition encasement during self-fitting of the interocclusal appliance 10.

Figure 7:
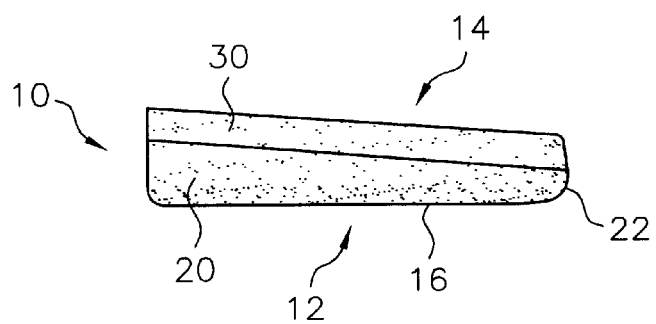
FIG. 7 is a side elevational view of the appliance, showing a downwardly, forwardly sloped buccal side wall of the base and a buccal peripheral wall of the preform.

The base 12 is substantially of uniform thickness throughout, e.g. 2 mm, and includes a generally planar occlusal face 16, an upwardly outwardly tapered lingual side wall 18 and a buccal side wall 20. The buccal side wall 20 slopes downwardly from the rear of the appliance toward its labial face 22 as shown in FIG. 7.

Pursuant to the invention, the impression preform 14 includes a shallow, e.g. between 2 and 2 mm deep, bight shaped centric relation pilot channel 24 configured to facilitate emplacement of the teeth of the user's maxillary arch at optimal position during and throughout self fitting of the appliance. The pilot channel includes a planar face 25. A footing having a height 26 extends from a horizontal upper surface of the base 12 to the channel face 25.

The shallow pilot channel 24 is defined by the face 25 and a pair of upwardly extending peripheral walls, i.e. a lingual peripheral wall 28, having an upper ridge 29, and a buccal peripheral wall 30, having an upper ridge 31. The buccal peripheral wall 30 includes a labial notch 32. The height of the buccal peripheral wall 30 above the face 25 is approximately between 2 and 2½ mm and is substantially uniform throughout (except at the notch 32). The height of the lingual peripheral wall is approximately 2 mm at the rear of the pilot channel and approximately 1 mm at a middle reduced height section 35.

It should be noted that the exterior surfaces of the lingual channel peripheral wall 28 and the buccal channel peripheral wall 30 are upwardly inwardly sloped from the top edge of the base side walls 18, 20. Similarly, an inner face 34 of the channel peripheral wall 28 and an inner face 36 of the channel peripheral wall 30 taper or slope at a draft angle from their respective ridges 29, 31, to the face 25 to facilitate self placement and registration of the maxillary teeth in the shallow pilot channel 24. The width of the channel face between the peripheral walls 28, 30 is approximately 9 mm. at the ends of the channel and approximately 6 mm. at its center. It should be understood that the dimensions herein are merely exemplary and differently sized appliances are appropriate, depending upon the dimensions of the user's dentition.

Figure 5:
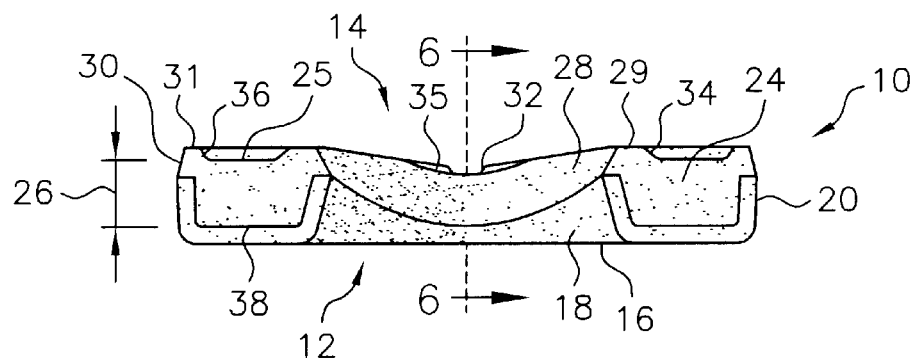
FIG. 5 is a rear elevational view of the interocclusal appliance, illustrating a tapered lingual side wall of the base.
Figure 6:
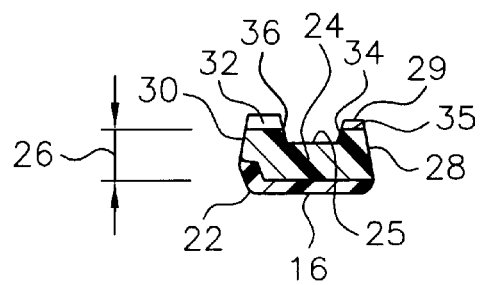
FIG. 6 is a sectional view through the interocclusal appliance, the same being taken substantially along the line 6—6 of FIG. 5.

It should also be noted that the lingual side wall 18 of the base tapers downwardly, toward the front of the appliance, where it meets the upper surface of the base, as can be more readily seen in FIG. 5 and FIG. 6.

The upper surface of the base and the opposed inner surfaces of the side walls 18, 20, all of which are bonded to the impression preform 14 when the preform is molded over the base, is designated by the reference numeral 38 in FIG. 5.

The height 26 of the preform footing varies from a maximum height, shown in FIG. 5 at the rear of the appliance, e.g. 6 to 6½ mm to a minimum height of approximately 4 mm at the front center of the appliance as shown in FIG. 6. The preform footing constitutes the primary source of impressionable material which forms around and conforms to the shape of the maxillary dentition during self-fitting.

It is significant that the thermoplastic material selected for the base has a softening temperature sufficiently above that of the impression preform material such that the thickness of the base is not significantly reduced as a result of the compressive forces applied during fitting.

Rheological characteristics of the base thermoplastic include a Vicat softening temperature (ASTM D1525) of at least 65° C., which is well above the temperatures reached during the fitting procedure, e.g. 40° C. to 46° C.

The mold bond between the base and the impression preform 14 (which is transformed into the maxillary encasement) is required to withstand the lateral and compressive stresses encountered during bruxing or clenching events at oral cavity temperatures.

In accordance with the present invention, the base 12 is formed by injection molding a thermoplastic resin having requisite characteristics into a base mold cavity. The molded base 12 is positioned in an occlusal appliance mold cavity and a thermoplastic resin having the requisite characteristics for the impression preform 14 is injected into the appliance mold cavity over the base 12 and unitarily bonds thereto.

Suitable resins for employment as the impression preform include an ethylene vinyl acetate (EVA) copolymer available from the Du Pont under the trademark ELVAX® having a vinyl acetate content of at least 25%. A preferred EVA copolymer is ELVAX®150 having a 33% vinyl acetate content by weight, a Vicat softening temperature of 36° C. and a Shore A hardness of 73.

Preferred embodiments of the invention may be fabricated in accordance with the following examples:

EXAMPLE No. 1

A base 12 was injection molded utilizing the following resin formulation:

| BASE RESIN | PERCENTAGE BY WEIGHT |
| --- | --- |
| ELVALOY ® 1609 AC EMA | 100% |

The ELVALOY® 1609 AC ethylene methyl acrylate copolymer (available from DuPont) was heated to a recommended molding temperature and injection molded into the base mold cavity. The ELVALOY® 1609 AC EMA copolymer contains approximately 9% by weight acrylate and exhibits a Vicat softening temperature of 70° C. and a Shore A hardness of 97.

The following thermoplastic resin was utilized as the impression preform material:

| PREFORM RESIN | PERCENTAGE BY WEIGHT |
| --- | --- |
| ELVAX ® 150 EVA copolymer | 100% |

The ELVAX®150 EVA was heated to a recommended molding temperature above its melting point and injection molded into an occlusal appliance mold cavity over the molded base positioned within the mold cavity. The unitary interocclusal appliance removed from the mold cavity exhibited a high adhesion bond between the base and the molded over impression preform, both before and after fitting.

The interocclusal appliance of EXAMPLE No. 1 was heated by immersion in boiling water for approximately 40 seconds, removed from the boiling water and immersed in water at or below room temperature for approximately 1 second. The appliance was then inserted into the oral cavity, with the maxillary occlusal surfaces seated in the shallow centric relation pilot channel.

Thereafter, biting pressure was applied and the maxillary teeth were impressed into the impression preform. The impression preform material flowed over, around and conformed to the shape of the surfaces of the maxillary dentition. Upon cooling, the impression preform was transformed into a reusable flexible maxillary encasement.

It was noted that due to the compressive forces applied during the fitting procedure, slight base deformation occurred in the nature of minor indentations in the occlusal face 16, however, the base thickness was not compromised, such that a minimum spacing between occlusal surfaces of at least the thickness of the base, e.g.

EXAMPLE No. 2

A base 12 was injection molded utilizing the following resin formulation:

| BASE RESIN | PERCENTAGE BY WEIGHT |
| --- | --- |
| PELLETHANE ® 2103 - 80 AEN TPU elastomer | 50% |
| ELVAX ® 750 EVA | 50% |

ELVAX®750 EVA comprises an ethylene vinyl acetate copolymer available from DuPont and having a 9% vinyl acetate content by weight and PELLETHANE®2103-80 AEN comprises a thermoplastic polyurethane elastomer available from Dow Chemical Co.

Equal amounts by weight of PELLETHANE®2103-80 AEN and ELVAX®750 were blended by conventional apparatus. The blend was heated to a suitable molding temperature and thereafter injection molded into the base mold cavity.

The molded base 12 was positioned in an occlusal appliance mold cavity and the following thermoplastic resin was utilized as the impression preform:

| PREFORM RESIN | PERCENTAGE BY WEIGHT |
| --- | --- |
| ELVAX ® 150 EVA | 100% |

The ELVAX®150 EVA was heated to a recommended molding temperature above its melting point and injection molded into the occlusal appliance mold cavity over the molded base.

The interocclusal appliance was removed from the mold cavity and exhibited a high adhesion bond between the base and the impression preform before and after fitting.

The interocclusal appliance of EXAMPLE No. 2 was heated by immersion in boiling water for approximately 40 seconds, removed from the boiling water and immersed in water at or below room temperature for approximately 1 second. The appliance was then inserted into the oral cavity, with the maxillary occlusal surfaces seated in the shallow centric relation pilot channel.

Thereafter, biting pressure was applied and the maxillary teeth were impressed into the impression preform. The impression preform material flowed over, around and conformed to the shape of the surfaces of the maxillary dentition. Upon cooling, the impression preform was transformed into a reusable flexible maxillary encasement.

Greater base deformation occurred during fitting than in Example 1, however, the base thickness was not compromised and a minimum spacing between occlusal surfaces of at least the thickness of the base, e.g. 2 mm. was maintained.

EXAMPLE No. 3

A base 12 was injection molded utilizing the following resin formulation:

| BASE RESIN | PERCENTAGE BY WEIGHT |
|---|---|
| ELVALOY ® 1609 AC EMA | 90% |
| ELVAX ® 750 EVA | 10% |

Ninety percent (90%) by weight of ELVALOY®1609 AC EMA was blended with ten percent (10%) by weight ELVAX®750 EVA with conventional blending apparatus. The blend was then heated to a suitable molding temperature and thereafter injection molded into the base mold cavity. The molded base 12 exhibited a Shore A hardness of 90.

The molded base 12 was then inserted into an occlusal appliance mold cavity and the following thermoplastic resin was utilized as the impression preform:

| PREFORM RESIN | PERCENTAGE BY WEIGHT |
|---|---|
| ELVAX ® 150 EVA | 100% |

The ELVAX®150 EVA was heated to a recommended molding temperature above its melting point and injection molded into the occlusal appliance mold cavity over the molded base.

The interocclusal appliance was removed from the mold cavity and exhibited a high adhesion bond between the base and the impression preform both before and after fitting.

The interocclusal appliance of EXAMPLE No. 3 was heated by immersion in boiling water for approximately 40 seconds, removed from the boiling water and immersed in water at or below room temperature for approximately 1 second. The appliance was then inserted into the oral cavity, with the maxillary occlusal surfaces seated in the shallow centric relation pilot channel.

Thereafter, biting pressure was applied and the maxillary teeth were impressed into the impression preform. The impression preform material flowed over, around and conformed to the shape of the surfaces of the maxillary dentition. Upon cooling, the impression preform was transformed into a reusable flexible maxillary encasement.

Slight base deformation occurred during fitting, somewhat greater than that of the base in EXAMPLE No. 1, however, less than the base deformation which occurred in EXAMPLE No. 2.

EXAMPLE No. 4

A base 12 was injection molded utilizing the following resin formulation:

| BASE RESIN | PERCENTAGE BY WEIGHT |
|---|---|
| ELVALOY ® 1609 AC EMA | 75% |
| ELVAX ® 750 EVA | 25% |

Seventy five percent (75%) ELVALOY®1609 AC EMA by weight is blended with 25% by weight ELVAX®750 EVA, utilizing conventional mixing apparatus. The blend was heated to a suitable molding temperature and thereafter injection molded into the base mold cavity. The molded base 12 exhibited a Shore A hardness of 92.

The molded base 12 was then inserted into an occlusal appliance mold cavity and the following thermoplastic resin was utilized as the impression preform:

| PREFORM RESIN | PERCENTAGE BY WEIGHT |
|---|---|
| ELVAX ® 150 EVA | 100% |

The ELVAX®150 EVA preform resin was heated to a suitable molding temperature and injection molded into an occlusal mold appliance cavity after the molded base had been positioned in the cavity. The interocclusal appliance removed from the mold cavity exhibited a high adhesion bond between the base and the molded over impression preform, both before and after the fitting.

The interocclusal appliance of EXAMPLE No. 4 was heated by immersion in boiling water for approximately 40 seconds, removal from the boiling water and immersed in water at or below room temperature for approximately 1 second. The appliance was then inserted into the oral cavity, with the maxillary occlusal surfaces seated in the shallow centric relation pilot channel.

Thereafter, biting pressure was applied and the maxillary teeth were impressed into the impression preform. The impression preform material flowed over, around and conformed to the shape of the surfaces of the maxillary dentition. Upon cooling, the impression preform was transformed into a reusable flexible maxillary encasement.

Slight base deformation occurred during fitting, e.g. approximately the same as occurred with respect to EXAMPLE No. 2. The base thickness was not compromised, however, and a minimum spacing between occlusal services of at least the thickness of the base was maintained.

EXAMPLE No. 5

A base 12 was injection molded utilizing the following resin formulation:

| BASE RESIN | PERCENTAGE BY WEIGHT |
|---|---|
| ELVALOY ® 1609 AC EMA | 50% |
| ELVAX ® 750 EVA | 50% |

Fifty percent (50%) ELVALOY® 1609 AC EMA by weight was blended with fifty percent (50%) by weight ELVAX®750 EVA, utilizing conventional mixing apparatus. The blend was heated to a suitable molding temperature and thereafter injection molded into the base mold cavity. The molded base 12 exhibited a Shore A hardness of 95.

The molded base 12 was then inserted into an occlusal appliance mold cavity and the following thermoplastic resin was utilized as the impression preform:

| PREFORM RESIN | PERCENTAGE BY WEIGHT |
|---|---|
| ELVAX ® 150 EVA | 100% |

The ELVAX®150 EVA preform resin was heated to a suitable molding temperature and injection molded into an occlusal mold appliance cavity after the molded base had been positioned in the cavity. The interocclusal appliance removed from the mold cavity exhibited a high adhesion bond between the base and molded over impression preform, both before and after the fitting.

The interocclusal appliance of EXAMPLE No. 5 was heated by immersion in boiling water for approximately 40 seconds, removed from the boiling water and immersed in water at or below room temperature for approximately 1 second. The appliance was then inserted into the oral cavity, with the maxillary occlusal surfaces seated in the shallow centric relation pilot channel.

Thereafter, biting pressure was applied and the maxillary teeth were impressed into the impression preform. The impression preform material flowed over, around and conformed to the shape of the surfaces of the maxillary dentition. Upon cooling, the impression preform was transformed into a reusable flexible maxillary encasement.

Some deformation of the base occurred during fitting, i.e. greater than the deformation which occurred with respect to EXAMPLE No. 2. The base thickness was not compromised, however, and a minimum spacing between occlusal surfaces of at least the thickness of the base was maintained.

EXAMPLE No. 6

A base 12 was injection molded utilizing the following resin formulation:

| BASE RESIN | PERCENTAGE BY WEIGHT |
|---|---|
| ELVALOY ® 1609 AC EMA | 90% |
| PELLETHANE ® 2103-80 AEN TPU | 10% |

Ninety percent (90%) ELVALOY®1609 AC by weight is blended with ten percent (10%) PELLETHANE®2103-80 AEN. The blend was heated to a suitable molding temperature and thereafter injection molded into the base mold cavity. Molded base 12 exhibited a Shore A hardness of 95.

The molded base 12 was then inserted into an occlusal appliance mold cavity and the following thermoplastic resin was utilized as the impression preform:

| PREFORM RESIN | PERCENTAGE BY WEIGHT |
|---|---|
| ELVAX ® 150 EVA | 100% |

The ELVAX®150 EVA preform resin was heated to a suitable molding temperature and injection molded into an occlusal mold appliance cavity after the molded base had been positioned in the cavity. The interocclusal appliance removed from the mold cavity exhibited a high adhesion bond between the base and molded over impression preform, both before and after the fitting.

The interocclusal appliance of EXAMPLE No. 6 was heated by immersion in boiling water for approximately 40 seconds, removed from the boiling water and immersed in water at or below room temperature for approximately 1 second. The appliance was then inserted into the oral cavity, with the maxillary occlusal surfaces seated in the shallow centric relation pilot channel.

Thereafter, biting pressure was applied and the maxillary teeth were impressed into the impression preform. The impression preform material flowed over, around and conformed to the shape of the surfaces of the maxillary dentition. Upon cooling, the impression preform was transformed into a reusable flexible maxillary encasement.

Slight base deformation occurred during fitting, i.e. less than the deformation which occurred with respect to EXAMPLE No. 1.

Other suitable base resin formulations comprise blends of ELVALOY® 1609 AC EMA and PELLETHANE® 2103-80 AEN TPU ranging between 10% to 50% TPU by weight. Additional base resin formulations may comprise linear low density polyethylene (LLDPE), low density polyethylene (LDPE) or blends of ELVAX 750 EVA and LLDPE or LDPE with the LLDPE or LDPE content ranging from 25% to 90% by weight.

It should be appreciated that the foregoing is merely exemplary and various other and alternate thermoplastic resins may be selected for use in accordance with the invention. The principal rheological and other attributes of the selected resins include a suitable softening temperature range for the impression preform resin which will not create temperature induced discomfort or damage to oral tissue, a softening temperature range and hardness of the base resin such that substantial deformation of the base does not occur during fitting and over prolonged usage.

An additional and significant characteristic upon which the selection of resins is predicated is the ability to obtain a unitary molded over bond between the base and the preform/maxillary dentition encasement which is well-suited to withstand the high shear and compression forces generated during bruxing and clenching events.

In this regard, it should be noted that in the foregoing examples, the surface 38 of the base over which the impression preform resin is molded may include a coating of a bonding agent or priming material or may be textured to augment the bond, all within the context of the present invention.

Also within the purview of the invention is the utilization of the interocclusal appliance in an inverted state, that is having the occlusal face 16 of the base in contact with maxillary occlusal surfaces and the mandibular dentition impressed in the impression preform.

Thus it will be seen that there is provided an interocclusal appliance which achieves the various aspects, features and considerations of the present invention and which is well-suited to meet the conditions of practical usage.

Since various possible embodiments might be made of the present invention and since various changes might be made in the exemplary embodiments shown herein, without departing from the spirit of the invention, it should be understood that all matter herein described or shown in the accompanying drawings should be interpreted as illustrative and not in a limiting sense.

Having thus described the invention there is claimed as new and desired to be secured by Letters Patent:

1. An interocclusal appliance for alleviation of the adverse effects of bruxing or clenching events, the appliance comprising a base and an impression preform unitarily bonded thereto, the base having a plan configuration of a dental arch and a generally planar occlusal face, the impression preform being bonded to an opposite face of the base, the impression preform including a bight shaped shallow centric relation pilot channel, the pilot channel having a generally planar face and a pair of spaced peripheral walls, the impression preform further including a footing having a height extending from the opposite face of the base to the face of the pilot channel, the impression preform comprising a resin having a Shore A hardness below 80 and a Vicat softening temperature, the base comprising a resin having a hardness of at least Shore A 80 and a Vicat softening temperature above that of the impression preform resin.

2. An interocclusal appliance for the alleviation of the adverse effects of bruxing or clenching events as constructed in accordance with claim 1 wherein the impression preform resin comprises an ethylene vinyl acetate copolymer having approximately 30% by weight vinyl acetate.

3. An interocclusal appliance for the alleviation of the adverse effects of bruxing or clenching events as constructed in accordance with claim 2 wherein the base resin comprises an ethylene methyl acrylate copolymer.

4. An interocclusal appliance for the alleviation of the adverse effects of bruxing or clenching events as constructed in accordance with claim 1 wherein the base resin comprises an ethylene methyl acrylate copolymer.

5. An interocclusal appliance for alleviation of the adverse effects of bruxing or clenching events as constructed in accordance with claim 4 wherein the ethylene methyl acrylate copolymer includes approximately 9% by weight acrylate.

6. An interocclusal appliance for alleviation of the adverse effects of bruxing or clenching events as constructed in accordance with claim 1 wherein the base resin comprises a thermoplastic polyurethane elastomer blended with an ethylene vinyl acetate copolymer.

7. An interocclusal appliance for the alleviation of the adverse effects of bruxing or clenching events as constructed in accordance with claim 1 wherein the base resin comprises an ethylene methyl acrylate copolymer blended with a thermoplastic selected from the group consisting of ethylene vinyl acetate copolymer and thermoplastic polyurethane elastomer.

8. An interocclusal appliance for the alleviation of the adverse effects of bruxing or clenching events as constructed in accordance with claim 1 wherein the pilot channel has a depth in the order of 2 mm.

9. An interocclusal appliance for the alleviation of the adverse effects of bruxing or clenching events as constructed in accordance with claim 1 wherein each peripheral wall includes a ridge and an inner face, the inner faces being sloped downwardly and inwardly from their respective ridges toward the face of the pilot channel.

10. An interocclusal appliance for the alleviation of the adverse effects of bruxing or clenching events as constructed in accordance with claim 1 wherein the face of the pilot channel is between approximately 6 mm to 9 mm wide.

11. An interocclusal appliance for the alleviation of the adverse effects of bruxing or clenching events as constructed in accordance with claim 1 wherein the height of the footing ranges from approximately 4 mm at the center of the pilot channel to at least 6½ mm at the rear of the pilot channel.

12. An interocclusal appliance for the alleviation of the adverse effects of bruxing or clenching events as constructed in accordance with claim 1 wherein the height of the footing is at least twice the distance between the occlusal face of the base and the opposite face of the base.

13. An interocclusal appliance for alleviation of the adverse effects of bruxing or clenching events, the appliance comprising a base and an impression preform unitarily bonded thereto, the base having a plan configuration of a dental arch and a generally planar occlusal face, the impression preform being bonded to an opposite face of the base, the impression preform including a bight shaped shallow centric relation pilot channel, the pilot channel having a generally planar face and a pair of spaced peripheral walls, the impression preform further including a footing having a height extending from the opposite face of the base to the face of the pilot channel, the height of the footing being at least twice the distance between the occlusal face of the base and the opposite face of the base.

14. An interocclusal appliance for the alleviation of the adverse effects of bruxing or clenching events as constructed in accordance with claim 13 wherein the impression preform comprises an ethylene vinyl acetate copolymer having approximately 30% by weight vinyl acetate and the base comprises an ethylene methyl acrylate copolymer having approximately 9% by weight acrylate and a Vicat softening temperature of at least 70° C.

15. An interocclusal appliance for the alleviation of the adverse effects of bruxing or clenching events as constructed in accordance with claim 13 wherein the pilot channel has a depth which is approximately the distance between the occlusal face of the base and the opposite face of the base.

16. An interocclusal appliance for the alleviation of the adverse effects of bruxing or clenching events as constructed in accordance with claim 13 wherein the channel width is approximately 4 times the distance between the occlusal face of the base and the opposite face of the base.

17. A method of fabricating an interocclusal appliance for alleviation of the adverse effects of bruxing or clenching events, the method comprising the steps of:

a) molding and appliance base from a resin having a Vicat softening temperature of at least 70° C. and a Shore A hardness of at least 80; and b) molding over the base an impression preform from a resin comprising an ethylene vinyl acetate copolymer having approximately 30% by weight vinyl acetate.

* * * * *